United States Patent
Terashima et al.

(10) Patent No.: US 11,064,923 B2
(45) Date of Patent: Jul. 20, 2021

(54) LIQUID SAMPLE MEASUREMENT DEVICE WITH REMOVABLE LANCET OR BIOSENSOR

(71) Applicant: PHC Holdings Corporation, Tokyo (JP)

(72) Inventors: Noriyoshi Terashima, Kanagawa (JP); Akio Nagao, Ehime (JP); Masataka Nadaoka, Ehime (JP); Yoshimasa Oda, Ehime (JP)

(73) Assignee: PHC Holdings Corporation, Tokyo (JP)

( * ) Notice: Subject to any disclaimer, the term of this patent is extended or adjusted under 35 U.S.C. 154(b) by 426 days.

(21) Appl. No.: 15/995,131

(22) Filed: Jun. 1, 2018

(65) Prior Publication Data

US 2018/0279933 A1    Oct. 4, 2018

Related U.S. Application Data

(63) Continuation of application No. 14/362,602, filed as application No. PCT/JP2012/008311 on Dec. 26, 2012, now Pat. No. 10,016,155.

(30) Foreign Application Priority Data

Dec. 26, 2011 (JP) .................. 2011-283196

(51) Int. Cl.
A61B 5/157     (2006.01)
A61B 5/00      (2006.01)
(Continued)

(52) U.S. Cl.
CPC ............ *A61B 5/157* (2013.01); *A61B 5/1411* (2013.01); *A61B 5/14532* (2013.01);
(Continued)

(58) Field of Classification Search
None
See application file for complete search history.

(56) References Cited

U.S. PATENT DOCUMENTS 5,307,263 A    4/1994   Brown
6,027,459 A    2/2000   Shain et al.
(Continued)

FOREIGN PATENT DOCUMENTS

CN    2108516 U    7/1992
CN    1455654 A    11/2003
(Continued)

OTHER PUBLICATIONS

English-machine translation of JP 2010-048623 from Google Patents, 22 pages, printed out on Aug. 6, 2020 (Year: 2020).*

(Continued)

*Primary Examiner* — Matthew Kremer
(74) *Attorney, Agent, or Firm* — Wenderoth, Lind & Ponack, L.L.P.

(57) ABSTRACT

This liquid sample measurement device is provided with: a lancet mounting part to and from which a lancet device having a skin contact section for puncturing skin can be attached and detached; a sensor mounting part to which a biosensor, which is spotted with blood that comes out from the punctured skin, can be attached; and a measurement part that uses the biosensor attached to the sensor mounting part to measure the amounts of substances in the blood. The liquid sample measurement device includes a feature that makes it necessary to replace a lancet device that has been attached to the lance mounting part and has punctured skin, each time a lancet device is used to puncture skin.

3 Claims, 13 Drawing Sheets

(51) Int. Cl.
  *A61B 5/15* (2006.01)
  *A61B 5/151* (2006.01)
  *A61B 5/145* (2006.01)
  *A61B 5/1486* (2006.01)

(52) U.S. Cl.
  CPC ...... *A61B 5/1519* (2013.01); *A61B 5/150022* (2013.01); *A61B 5/15087* (2013.01); *A61B 5/15111* (2013.01); *A61B 5/15117* (2013.01); *A61B 5/150175* (2013.01); *A61B 5/15194* (2013.01); *A61B 5/150358* (2013.01); *A61B 5/150427* (2013.01); *A61B 5/150503* (2013.01); *A61B 5/6898* (2013.01); *A61B 5/1486* (2013.01); *A61B 5/150793* (2013.01); *A61B 2560/0266* (2013.01); *A61B 2562/0295* (2013.01); *A61B 2562/08* (2013.01)

(56) References Cited

U.S. PATENT DOCUMENTS

| | | |
|---|---|---|
| 6,071,249 A | 6/2000 | Cunningham et al. |
| 6,071,251 A | 6/2000 | Cunningham et al. |
| 6,093,156 A | 7/2000 | Cunningham et al. |
| 6,206,841 B1 | 3/2001 | Cunningham et al. |
| 6,306,104 B1 | 10/2001 | Cunningham et al. |
| 6,837,858 B2 | 1/2005 | Cunningham et al. |
| 7,252,804 B2 | 8/2007 | Miyashita et al. |
| 7,691,071 B2 | 4/2010 | Kojima et al. |
| 7,758,517 B2 | 7/2010 | Kojima et al. |
| 7,841,993 B2 | 11/2010 | Kojima et al. |
| 7,905,843 B2 | 3/2011 | Kojima et al. |
| 7,998,087 B2 | 8/2011 | Amano et al. |
| 8,052,707 B2 | 11/2011 | Karbowniczek et al. |
| 8,062,320 B2 | 11/2011 | Ono et al. |
| 8,118,756 B2 | 2/2012 | Kojima et al. |
| 8,221,335 B2 | 7/2012 | Amano et al. |
| 8,235,914 B2 | 8/2012 | Kojima et al. |
| 8,357,107 B2 | 1/2013 | Draudt et al. |
| 8,551,017 B2 | 10/2013 | Kojima et al. |
| 2002/0169393 A1 | 11/2002 | Cunningham et al. |
| 2003/0050537 A1* | 3/2003 | Wessel ............... A61B 5/6887 600/300 |
| 2003/0144608 A1 | 7/2003 | Kojima et al. |
| 2003/0191415 A1* | 10/2003 | Moerman ........ A61B 5/150022 600/584 |
| 2004/0133125 A1 | 7/2004 | Miyashita et al. |
| 2004/0138588 A1 | 7/2004 | Saikley et al. |
| 2005/0222599 A1 | 10/2005 | Czernecki et al. |
| 2005/0240119 A1 | 10/2005 | Draudt et al. |
| 2006/0108218 A1 | 5/2006 | Gephart et al. |
| 2007/0123782 A1 | 5/2007 | Connolly et al. |
| 2008/0057484 A1 | 3/2008 | Miyata et al. |
| 2008/0058631 A1 | 3/2008 | Draudt et al. |
| 2008/0195133 A1 | 8/2008 | Zhong et al. |
| 2008/0200838 A1* | 8/2008 | Goldberger ...... A61B 5/150633 600/583 |
| 2009/0069717 A1 | 3/2009 | Kojima et al. |
| 2009/0069718 A1 | 3/2009 | Kojima et al. |
| 2009/0069719 A1 | 3/2009 | Kojima et al. |
| 2009/0093694 A1 | 4/2009 | Kojima et al. |
| 2009/0093736 A1 | 4/2009 | Kojima et al. |
| 2009/0105615 A1 | 4/2009 | Kojima et al. |
| 2009/0177117 A1 | 7/2009 | Amano et al. |
| 2009/0198265 A1 | 8/2009 | Ono et al. |
| 2010/0036407 A1 | 2/2010 | Fowler et al. |
| 2010/0072270 A1 | 3/2010 | Creaven et al. |
| 2010/0087754 A1 | 4/2010 | Rush et al. |
| 2010/0168775 A1 | 7/2010 | Karbowniczek et al. |
| 2010/0198107 A1* | 8/2010 | Groll ................ A61B 5/15182 600/583 |
| 2010/0198246 A1 | 8/2010 | Ono et al. |
| 2010/0234868 A1 | 9/2010 | Ono et al. |
| 2011/0040210 A1 | 2/2011 | Kojima et al. |
| 2011/0257498 A1 | 10/2011 | Amano et al. |
| 2011/0313350 A1 | 12/2011 | Krulevitch et al. |
| 2012/0050047 A1* | 3/2012 | Kim ....................... H04L 67/12 340/573.1 |
| 2012/0089051 A1 | 4/2012 | Draudt et al. |
| 2013/0200140 A1 | 8/2013 | Kawabata et al. |

FOREIGN PATENT DOCUMENTS

| | | |
|---|---|---|
| CN | 1514700 A | 7/2004 |
| CN | 1524495 A | 9/2004 |
| CN | 101132733 A | 2/2008 |
| CN | 101374457 A | 2/2009 |
| EP | 449525 A1 | 10/1991 |
| GB | 2479984 A | 11/2011 |
| JP | 2004-290385 A | 10/2004 |
| JP | 2005-518858 A | 6/2005 |
| JP | 2005-205096 A | 8/2005 |
| JP | 2007-532266 A | 11/2007 |
| JP | 2008-111827 A | 5/2008 |
| JP | 2009-195359 A | 9/2009 |
| JP | 2010-048623 A | 3/2010 |
| JP | 2010-524558 A | 7/2010 |
| WO | 2006/118224 A1 | 11/2006 |
| WO | 2010/098931 A1 | 9/2010 |
| WO | 2011/115028 A1 | 9/2011 |

OTHER PUBLICATIONS

English-machine translation of JP 2004-290385 from Google Patents, 17 pages, printed out on Aug. 6, 2020 (Year: 2020).*
International Search Report of Int'l Appln. No. PCT/JP2012/008311 dated Feb. 26, 2013.
Extended European search report from the corresponding European Patent Application No. 12863840.0 dated Sep. 23, 2014.
Office Action from the corresponding Chinese Patent Application No. 201280061270.2 dated Jul. 3, 2015.
Notice of Allowance from the corresponding Japanese Patent Application No. 2013-551247 dated Oct. 27, 2015.

* cited by examiner

LIQUID SAMPLE MEASUREMENT DEVICE WITH REMOVABLE LANCET OR BIOSENSOR

PRIORITY

This application is a continuation application of and claims priority to U.S. application Ser. No. 14/362,602 filed on Jun. 4, 2014, which is a National Stage Application and claims priority under 35 U.S.C. § 120 and 35 U.S.C. § 365 of International Application PCT/JP2012/008311, with an international filing date of Dec. 26, 2012 which claims priority to Japanese Patent Application No. 2011-283196 filed on Dec. 26, 2011. The entire disclosures of U.S. application Ser. No. 14/362,602 International Application PCT/JP2012/008311 and Japanese Patent Application No. 2011-283196 are hereby incorporated herein by reference.

TECHNICAL FIELD

The present invention relates to a liquid sample measurement device which measures biological information such as blood glucose concentration and lactic acid value from living subjects.

BACKGROUND ART

An arrangement where a test strip port 101 and lancet device 102 are configured on a same end of a device main body 100, as shown in FIG. 13, is well known, as the liquid sample measurement device. The liquid sample measurement device does not force users to perform complicated operations, but enables the users to perform a one-hand operation. Further, because a puncturing process and a measuring process can be performed closely, the liquid sample measurement device is characterized in realizing a small movement by the users (for example, see Patent Literature 1: Japanese Unexamined Patent Application Publication (Translation of PCT Application) No. 2007-532266).

On the other hand, in medical institutions, disposal lancet devices are often used for puncturing in order to prevent blood infection. The disposal lancet devices cannot be reused after puncturing and are disposed (for example, see Patent Literature 2: Japanese Unexamined Patent Application Publication (Translation of PCT Application) No. 2005-518858 and Patent Literature 3: Japanese Unexamined Patent Application Publication (Translation of PCT Application) No. 2010-524558).

Also, puncturing needle cartridges which are equipped to devices for puncturing have been disclosed. The puncturing needle cartridges have structures not allowing it to be reused after puncturing, and are disposed (for example, see Patent Literature 4: International Patent Application Publication No. WO/2006/118224).

The above mentioned conventional liquid sample measurement device is arranged such that a depth controlling structure 103 of a lancet device 102 makes contact with a skin surface.

The present invention is presented in considering the above mentioned problems, and has objective to provide a liquid sample measurement device having an element being replaceable, at which liquid sample such as blood of a living subject adheres.

SUMMARY

A liquid sample measurement device of the present arrangement includes a lancet wearing part to which a lancet device is attachable, the lancet device including a skin contacting part for puncturing a skin; a sensor wearing part to which a biosensor is detachable, the biosensor on which blood from the skin by puncturing is deposited; a measuring section which measures an amount of a substance in the blood by using the biosensor being attached to the sensor wearing part. Each time when the lancet device performs to puncture the skin, it is needed to replace the lancet device which is attached to the lancet wearing part and which has punctured the skin.

According to the above mentioned liquid sample measurement device, because an element at which the blood of a living subject adheres is easily replaced, safety is enhanced while convenience is enhanced. Further, according to the liquid sample measurement device, replacement of the element at which a liquid sample such as the blood of the living subject adheres can be encouraged.

BRIEF DESCRIPTION OF THE DRAWINGS

FIG. 1A is a front view, FIG. 1B is a side view, and FIG. 1C is a lower side view;

FIG. 4A is a sectional view showing an embodiment as an example, and FIG. 4B is a sectional view showing a different embodiment;

DETAILED DESCRIPTION

Hereinafter, embodiments of the liquid sample measurement device to which the present invention is applied are described with reference to the drawings. It will be apparent to those skilled in the art from this disclosure that the following descriptions of the embodiments are provided for illustration only and not for the purpose of limiting the invention as defined by the appended claims and their equivalents.

First Embodiment

Figures 1A, 1B:
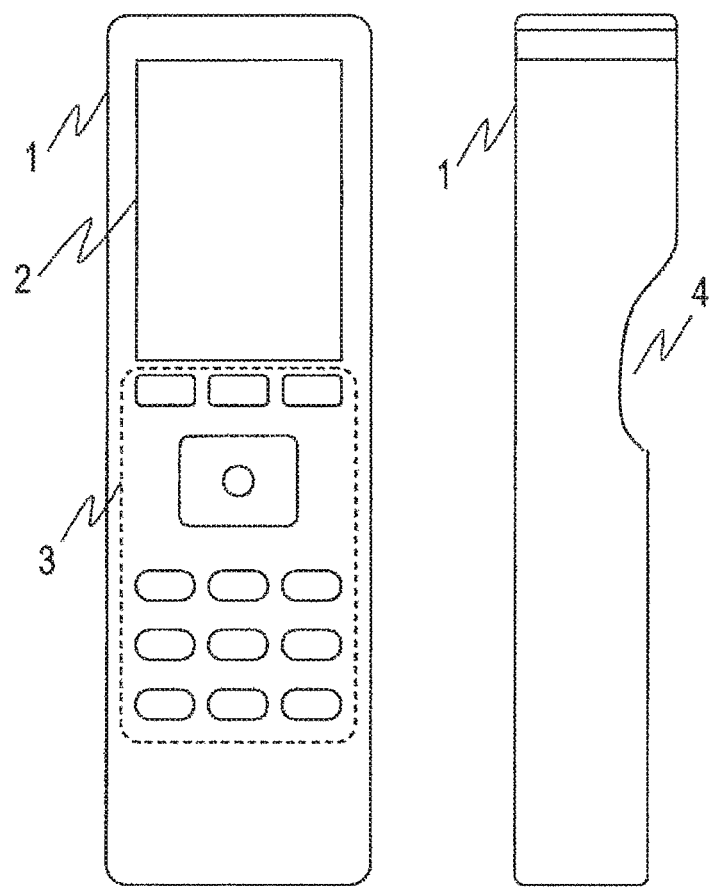
FIGS. 1A to 1C are view showing a configuration of a liquid sample measurement device of an embodiment of the present invention.
Figure 1C:
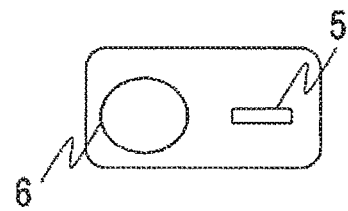

FIGS. 1A to 1C are the view showing the arrangement of liquid sample measurement device of a first embodiment.

Figure 2:
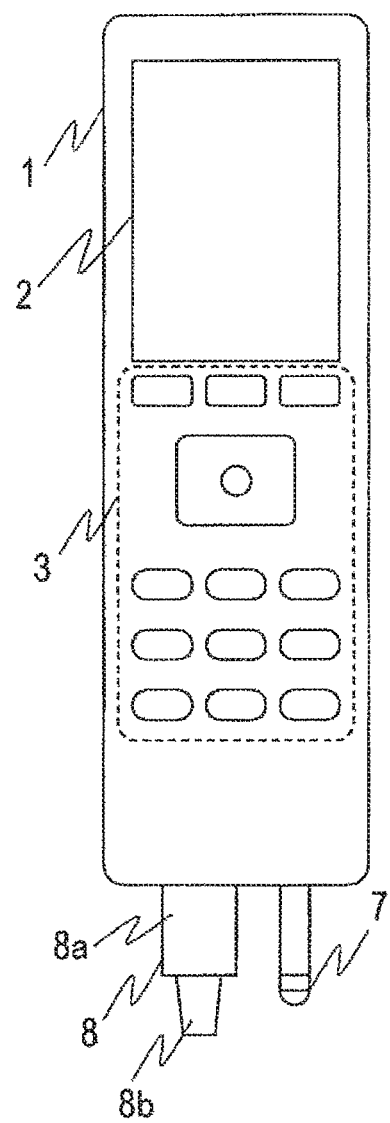
FIG. 2 is a view showing the liquid sample measurement device with a biosensor and a lancet device.

FIG. 1A is the front view of the device main body 1. FIG. 1B is the side view of the device main body 1. FIG. 1C is the lower side view of the device main body 1. As shown in FIGS. 1A to 1C, on a front side of the device main body 1, a display section 2 and an input section 3 are configured. On a back side of the device main body 1, a finger position part 4 on which a user put a finger when holding the device main body 1 is configured. On a lower side of the device main body 1, a sensor wearing part 5 and a lancet wearing part 6 are configured. As shown in FIG. 2, a biosensor 7 which is disposable is equipped on the sensor wearing part 5. A lancet device 8 which is disposable is equipped on the lancet wearing part 6.

The biosensor 7 and lancet device 8 are disposable elements which are required to be replaced after the user uses them one time. These two elements are manually equipped on the device main body 1 by the user. Also, these two elements are detached from the device main body 1 by the user.

The sensor wearing part 5 includes an arrangement which the biosensor 7 on which blood from a skin by puncturing is deposited can be equipped. The sensor wearing part 5 has an opening which extends to an inner side of the device main body 1 to accommodate the biosensor 7. The opening has an inner diameter being equal to or slightly larger than an outer diameter of the biosensor 7. The opening has a shape through which a part of the biosensor 7 can pass.

An end of the biosensor 7 which is inserted to the sensor wearing part 5 is sustained by a connector 5a which constitutes a part of the sensor wearing part 5. At this time, an opposite end (the other end) to the end sustained by the connector 5a sticks out of the device main body 1. In this state, the blood is deposited on the other end of the biosensor 7. When the biosensor 7 is disposed, the user holds the biosensor 7 and separates from the device main body 1 by pulling out of the sensor wearing part 5.

The lancet wearing part 6 includes an arrangement where the lancet device 8 including a skin contacting part for puncturing the skin is detachable. The lancet wearing part 6 is concaved in a direction towards the inner side of the device main body 1 for accommodating the lancet device 8. The concave has a shape to accommodate a first body 8a of the lancet device 8. This concave has an inner diameter being equal to or slightly larger than an outer diameter of the first body 8a.

The lancet device 8 is in a state where the lancet wearing part 6 is inserted and the end of the first body 8a is in contact with a bottom part of the concave. In this state, per the lancet device 8, a periphery of the first body 8a is sustained by an engaging part, such as a rubber, which is configured on an inner wall of the concave. At this time, the opposite side of the first body 8a sticks out of the device main body 1. Further, the lancet device 8 includes a second body 8b on the tip of the first body 8a. Puncturing is performed by contacting a tip of the second body 8b to the skin. When the lancet device 8 is disposed, the user holes the lancet device 8 and easily separates from the device main body 1 by pulling out of the lancet wearing part 6.

With the liquid sample measurement device, the biosensor 7 and the lancet device 8 as elements on which the blood adheres can be easily replaced by arranging in the way mentioned above. Therefore, the convenience is enhanced because measuring is continuously performed on a plurality of the subjects by replacing continuously the disposable elements.

It is fine that a cover which is transparent or translucent to cover an opening part of the concave of the lancet wearing part 6. The cover is detachable equipped with the device main body 1. It is fine that the cover covers at least the opening part of the concave. For example, the cover can entirely cover the device main body 1. Also, the cover can cover from a side surface having the lancet wearing part 6 to the input section 3. Further, the cover can cover only the side surface having the lancet wearing part 6. This cover is made of an elastic material such as rubber. When the lancet device 8 is not equipped on the device main body 1, the cover covers the opening part of the lancet wearing part 6. The lancet device 8 is equipped; this cover is pushed to extend towards the inner side of the concave. A part of this concave which is pushed to extend is between the inner wall of the concave and the lancet device 8, and functions as the engaging part.

Here, as shown in FIG. 2, the sensor wearing part 5 and the lancet wearing part 6 are configured such that the biosensor 7 and the lancet device 8 are configured adjacent to each other on the same side. In other words, a place for puncturing the skin and a place at which the blood is deposited are closely located in the liquid sample measurement device. This allows the user to puncture the skin by the lancet device 8 and spot the blood to the biosensor 7 smoothly with little movement in a short period of time.

By the way, the locations of the sensor wearing part 5 and the lancet wearing part 6 are not limited to a horizontal alignment as shown in FIGS. 1A to 1C. The locations of the sensor wearing part 5 and the lancet wearing part 6 can be a vertical alignment or a diagonal alignment, as long as on the same side surface.

For example, when the user is a nurse who measures blood of a patient, the user holds by one hand the device main body 1, and holds a finger of the patient by the other hand. Then, after puncturing by nearing the device main body 1 to the finger of the patient, the user lightly squeezes the blood by the hand holding the finger of the patient, while the device main body 1 stays in the same place. Then, depositing the blood can be performed by sliding the device main body 1 to locate the biosensor 7 at the place where the blood from the finger of the patient is squeezed.

Further, the biosensor 7 and the lancet device 8 are closely configured on the same side surface, and are equipped to stick out from the device main body 1. By this, it has an effect in reducing a chance of the blood squeezed from the skin by puncturing to be deposited by mistake on the device main body 1.

At this time, relationship of length for which the biosensor 7 and the lancet device 8 stick out of the device mail body is regulated, as follows. Namely, it is preferable that the tip of the biosensor sticks out longer than the tip of the lancet device 8. This is related to a method for puncturing of the lancet device 8 being disposable.

It will be discussed later, but puncturing is performed by urging a main body of the lancet device 8 onto the skin. It is same even when the lancet device 8 is equipped on the device main body 1. Thus, the user performs moving the lower surface of the device main body 1 in a state in which the biosensor 7 and the lancet device 8 are equipped towards the subject for puncturing.

At this time, the lancet device 8 is shorter because the second body 8b is slid into the first body 8a. For this reason, if the tip of the biosensor 7 exists closer to the skin side than the first body 8a, the biosensor 7 will collides with the skin strongly with momentum of puncturing and it will be possible that the biosensor 7 is damaged. Accordingly, the relationship in sticking out is defined.

However, when the biosensor 7 and the lancet device 8 equipped on the device main body 1 are located with ample distance there between, it is fine that the tip of the biosensor sticks out longer than the tip of the first body 8a of the lancet device 8. For example, when collecting blood of the tip of the finger by puncturing by using the lancet device 8 while stretching out the finger, it is fine as long as the biosensor 7 equipped on the device main body is apart for a size of one finger from the lancet device 8. By this, it is possible to avoid the collision of the biosensor to the finger of the patient when puncturing.

Figure 4A:
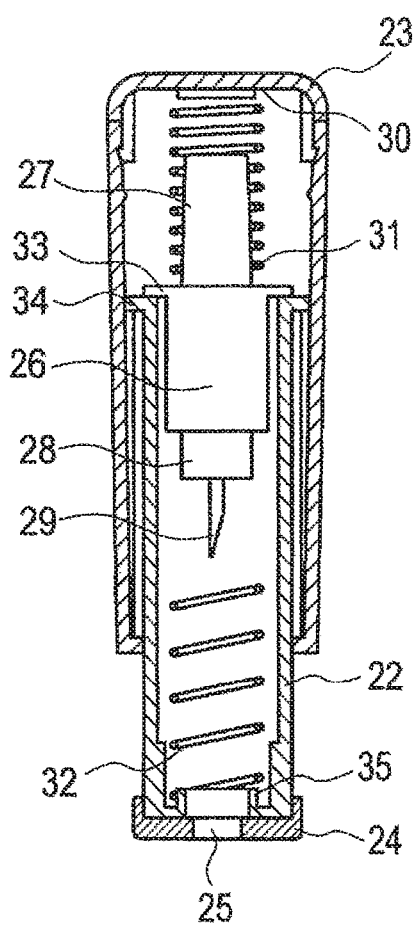
FIGS. 4A and 4B are a sectional view of the lancet device.
Figure 4B:
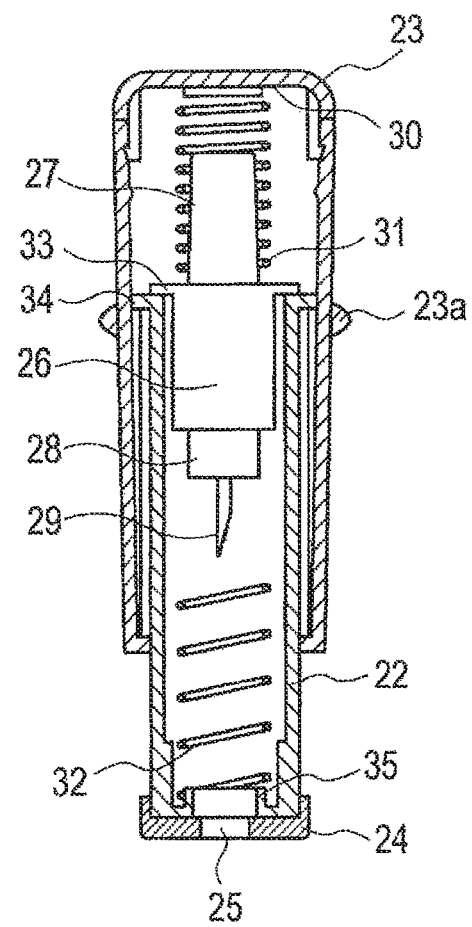

Next, the finger position part 4, as shown in FIG. 4B will be described. As shown in the figure, the finger position part 4 has a large shape of a basin towards the side of the lancet wearing part 6 of the device main body 1. By this, the finger position part 4 is shaped to receive a force towards the lancet wearing part 6. When the user holds the device main body 1, the user put the finger on the finger position part 4. When the user performs puncturing, the force is transmitted to the device main body 1 as the finger catches the basin.

Figure 3:
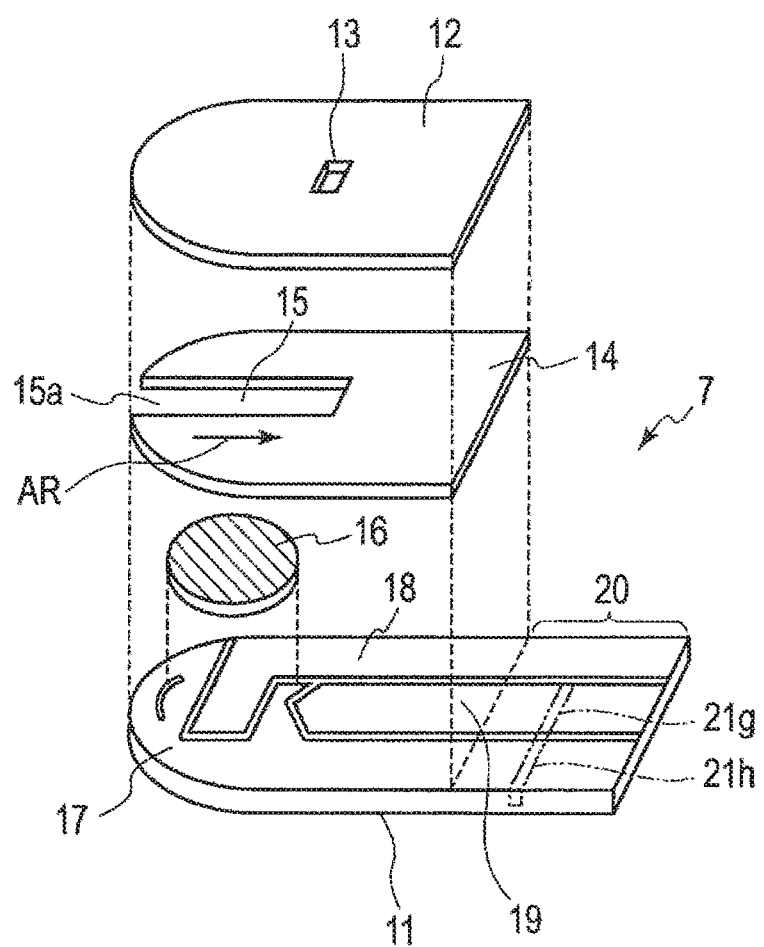
FIG. 3 is an exploded diagrammatic view of the biosensor.

Next, the biosensor which is disposable and equipped to the liquid sample measurement device is described by referring to FIG. 3. FIG. 3 is an exploded diagrammatic view showing the biosensor 7 equipped to the sensor wearing part 5 of the device main body 1.

The biosensor 7 includes an insulated substrate 11 (hereinafter simply "substrate 11") made of polyethylene terephthalate or the like. A surface of the substrate 11 has a conductive layer. The conductive layer is made, for example, of noble metal, such as gold, and palladium, or conductive material, such as carbon and the like. Also, the biosensor 7 includes an insulated substrate 12 on an upper surface thereof. The substrate 12 has an air opening 13 at a center part thereof. Between the substrate 11 and the substrate 12, a spacer 14 including a notch part is inserted. The biosensor 7 is made integrally of the substrate 11, the spacer 14, and the substrate 12.

A counter electrode 17, a measurement electrode 18, and a detection electrode 19 are formed by the conductive layer on the substrate 11 which is divided by slits. Each of the electrodes 17, 18, and 19 are at least partially formed on the substrate 11. Also, each of the electrodes 17, 18, and 19 can be connected by lead wire to the liquid sample measurement device, in a state where the biosensor 7 is equipped on the device main body 1.

The spacer 14 is configured to cover the counter electrode 17, the measurement electrode 18, and the detection electrode 19 on the substrate 11. A sample supply route 15 is formed by a notch part which is rectangular and which is on a front edge and a center of the spacer 14. Also, sample liquid on a sample depositing part 15a of the sample supply route is suctioned towards an air opening 13 of the substrate 12 (in a direction of an arrow AR in FIG. 3).

The reagent layer 16 has a size and a shape to cover the counter electrode 17, the measurement electrode 18, and the detection electrode 19 which are exposed from the notch part of the spacer 14.

Oxidation reduction enzyme and electron acceptor are included in the reagent layer 16. The oxidation reduction enzyme and the electron acceptor are dissolved and react with the liquid sample (in the present embodiment, blood from a human body) which is suctioned by the sample supply route 15. After the reaction, the liquid sample measurement device electrochemically oxidizes the electron acceptor, which has been reduced. The liquid sample measuring device measures the biological information (in the present embodiment, the blood glucose concentration in the blood) in the liquid sample on the basis of the electric current obtained by the oxidation. This chain of the reaction is read by electric current with the electrochemical changes by the measurement electrode 18 and the detection electrode 19.

Also, an identifying part 20 is a member which identifies differences in output characteristic depending on kinds and production lot of the biosensor 7 by the device main body 1. A combination of slit 21g and a slit 21h are configured at a part corresponding to the identifying part 20 of the counter electrode 17 and the detection electrode 19. By this, the device main body 1 can identify the difference of the electrical output characteristic of the biosensor 7.

The counter electrode 17, the measurement electrode 18, the counter electrode 17, and detection electrode 19 are arranged in the order from the sample depositing part 15a in the flow direction of the liquid sample (arrow AR) on the substrate of the biosensor 7. The configuration of the counter electrode 17 and the measurement electrode 18 can be switched.

Also, there is a prescribed distance between the measurement electrode 18 and the detection electrode 19 in the direction of the liquid sample flowing. By this, the detection electrode 19 can identify whether or not the liquid sample is surely and adequately suctioned.

Next, the lancet device 8 which is equipped on the liquid sample measurement device is described by referring to FIGS. 4A and 4B. FIG. 4A is a sectional view of the lancet device 8 which is equipped on the lancet wearing part 6 of the main body 1. The lancet device 8 itself is categorized as a disposable type, as the user can use for puncturing.

As described above, according to Patent Literature 2, of the lancet device 8, a wing 33 of a piston 26 is on an upper edge 34 of a sleeve 22 (the second body 8b) by urging of a drive spring 31. In this way, the piston 26 having a puncturing chip 29 is kept at a still position.

When the user locates the end of the second body 8b on the subject for puncturing, and pushes a push element 23 (the first body 8a) to the subject for puncturing, a drive spring 31 is compressed until a surface-in-use 30 of the push element 23 abuts a push rod 27 of the piston 26. When the push element 23 is further compressed, the wing 33 of the piston 26 is broken. Then, a fin 28 of the piston 26 is in contact with an internal limiting part 35 which limits depth of puncturing. In this state, the puncturing chip 29 passes through an opening 25 of a cap 24. By this, the puncturing chip 29 comes down to a prescribed depth defined by a thickness of the cap 24, and punctures the skin. In other words, puncturing is performed by locating the cap 24 on the skin and pushing from the other side towards the skin. Therefore, the cap 24 is a skin contact part which is arranged to be contact with a place for puncturing.

Next, a returning spring 32 pulls back the piston 26 which includes the puncturing chip 29. And then, the piston 26 moves to a second still position which is in the sleeve 22. The lancet device 8 cannot be reused, after the wing 33 of the piston 26 is broken.

FIG. 4B shows a convex belt 23a configured around the push element 23 of the lancet device 8. The convex belt 23a is used for holding more strongly, when the lancet device 8 is equipped on the lancet wearing part 6. In corresponding to the lancet device 8, it is fine to include a convex part or a concave part, which is engaged with the convex belt 23a, on an inner wall of a concave of the lancet wearing part 6.

Figure 5:
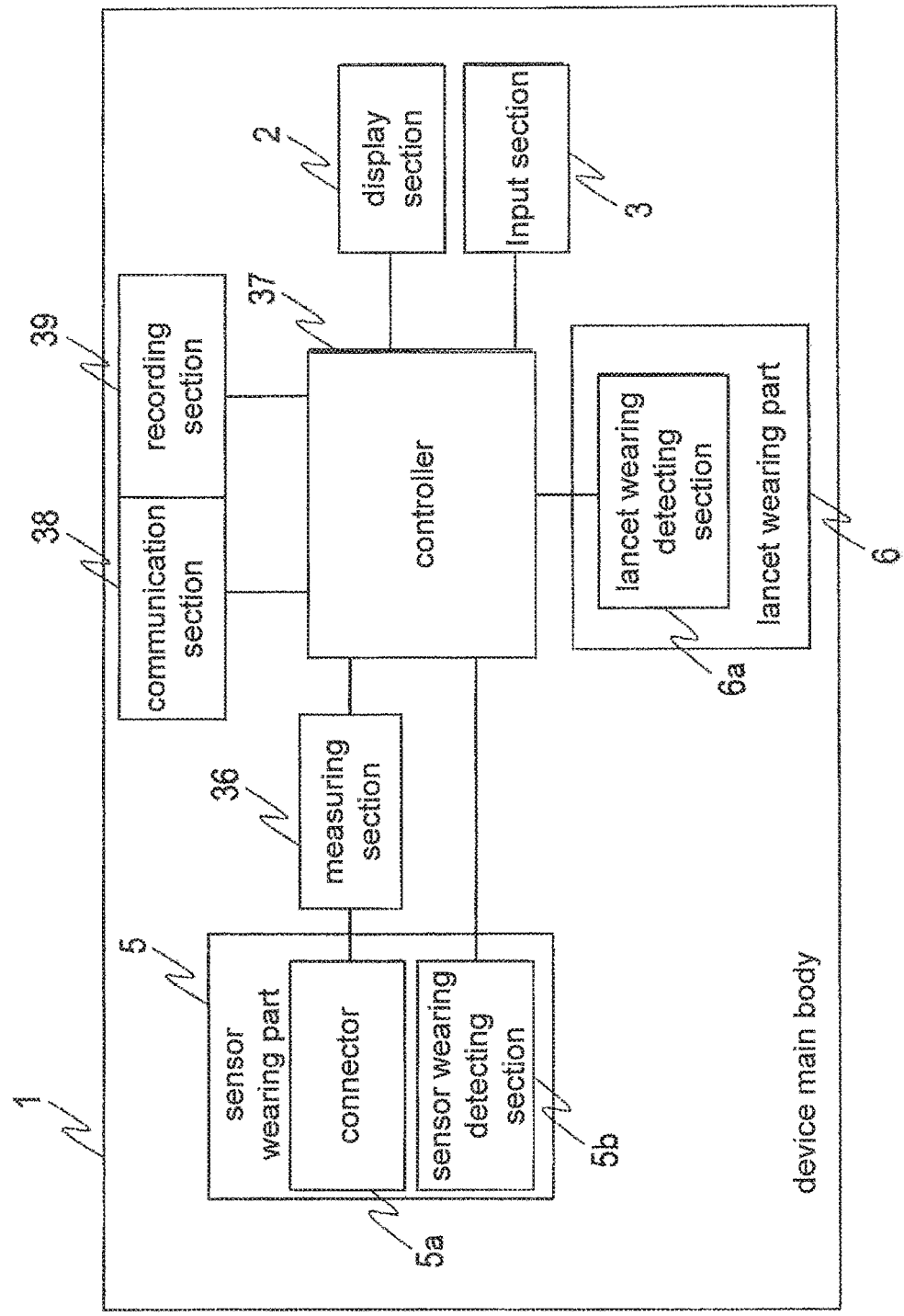
FIG. 5 is a block diagram of the liquid sample measurement device.

Next, constituent elements of the liquid sample measurement device is described by referring to FIG. 5. FIG. 5 is a block diagram showing the liquid sample measurement device. As shown in FIG. 5, in the device main body 1, the sensor wearing part 5, the lancet wearing part 6, a measuring section 36, a controller 37, the display section 2, the input section 3, a communication section 38, and a recording section 39 are configured.

Further, in the sensor wearing part 5, the connector 5a, and the sensor wearing detecting section 5b are configured. The connector 5a is connectable to the counter electrode 17, the measurement electrode 18, and the detection electrode 19 of the biosensor 7, when the biosensor 7 is equipped. The sensor wearing detecting section 5b detects whether or not the biosensor 7 is equipped on the sensor wearing part 5.

Instead of the sensor wearing detecting section 5b, it is fine to detect whether or not the biosensor 7 is equipped on the sensor wearing part 5 by a connection of the connector 5a to the biosensor 7.

Also, a lancet wearing detecting section 6a is configured in the lancet wearing part 6 to detect whether or not the lancet device 8 is equipped.

The measuring section 36 detects blood glucose concentration of the blood which is deposited on the biosensor 7 equipped on the lancet wearing part 6 in response to an instruction from the controller 37. For example, when the blood is deposited on the biosensor 7, electric voltage or electric current is applied to each of the electrodes of the biosensor 7 via the connector 5a. The measuring section 36 measures the blood glucose concentration in the blood from electric voltage or electric current as a response of the application of the electric voltage.

The controller 37 controls the liquid sample measurement device entirely. Specifically, information is input to the controller 37 from the sensor wearing detecting section 5b, the lancet wearing detecting section 6a, and the measuring section 36. The controller 37 instructs the measuring section 36 and the display section 2, and the communication section 38, on the basis of the input information.

The display section 2 works in response to the instruction from the controller 37. The display section 2 displays the blood glucose concentration as the biological information measured by the measuring section 36. Also, the display section 2 also displays various information for the user.

The input section 3 is a device to which information such as an instruction of how to perform and identification number is input. The input section 3, for example, is a button configured on the device main body 1. Alternatively, the input section 3 is an optical reading device such as a barcode reader. Alternatively, the input section 3 can be an input by wireless communication or voice recognition such as RF-ID. The input section 3 of the present embodiment is equipped with a plurality of devices. Also, the information input to the input section 3 is transmitted to the controller 37.

The communication section 38 performs data transmission and reception with other devices, such as personal computers, by receiving the instruction from the controller 37, by using the wireless or the wired communication means. For example, the communication section 38 transmits to other devices the identification number input to the input section 3 and the blood glucose concentration measured by the measuring section 36. Also, the communication section 38 receives a list of the identification number from other devices.

The recording section 39 receives the measurement result transmitted from the measuring section 36, the information input by the input section 3, the information received by the communication section 38, and the like via the controller 37, and records. The recording and playing the data to the recording section 39 is controlled by the controller 37.

The sensor wearing detecting section 5b and the lancet wearing detecting section 6a, when detecting that the biosensor 7 and the lancet device 8 are equipped respectively, transmit to the controller 37. Detection means of equipping is, for example, an electrical switch which is mechanical and detects equipping by conduction of the electrical switch made by being pushed while the object is equipped. The detection means of equipping can be any means, as long as the means detects existence of the object and transmits, such as an optical sensor.

The liquid sample measurement device like this includes arrangement, which requires the lancet device equipped to the lancet wearing part 6 and performing puncturing the skin, to be replaced after each time when puncturing the skin by the lancet device 8 is performed. The arrangement, as discussed hereinafter, includes not performing the next measuring, until the lancet device 8 is replaced after the measuring section 36 measures. Also, the arrangement includes not recording the measured result to the recording section 39, until the lancet device 8 and the biosensor 7 are replaced. The arrangement includes displaying on the display section 2 the measurement result and information persuading replacing the lancet device 8 and the biosensor 7, and keeps displaying these information until the lancet device 8 and the biosensor 7 are replaced.

Figure 6:
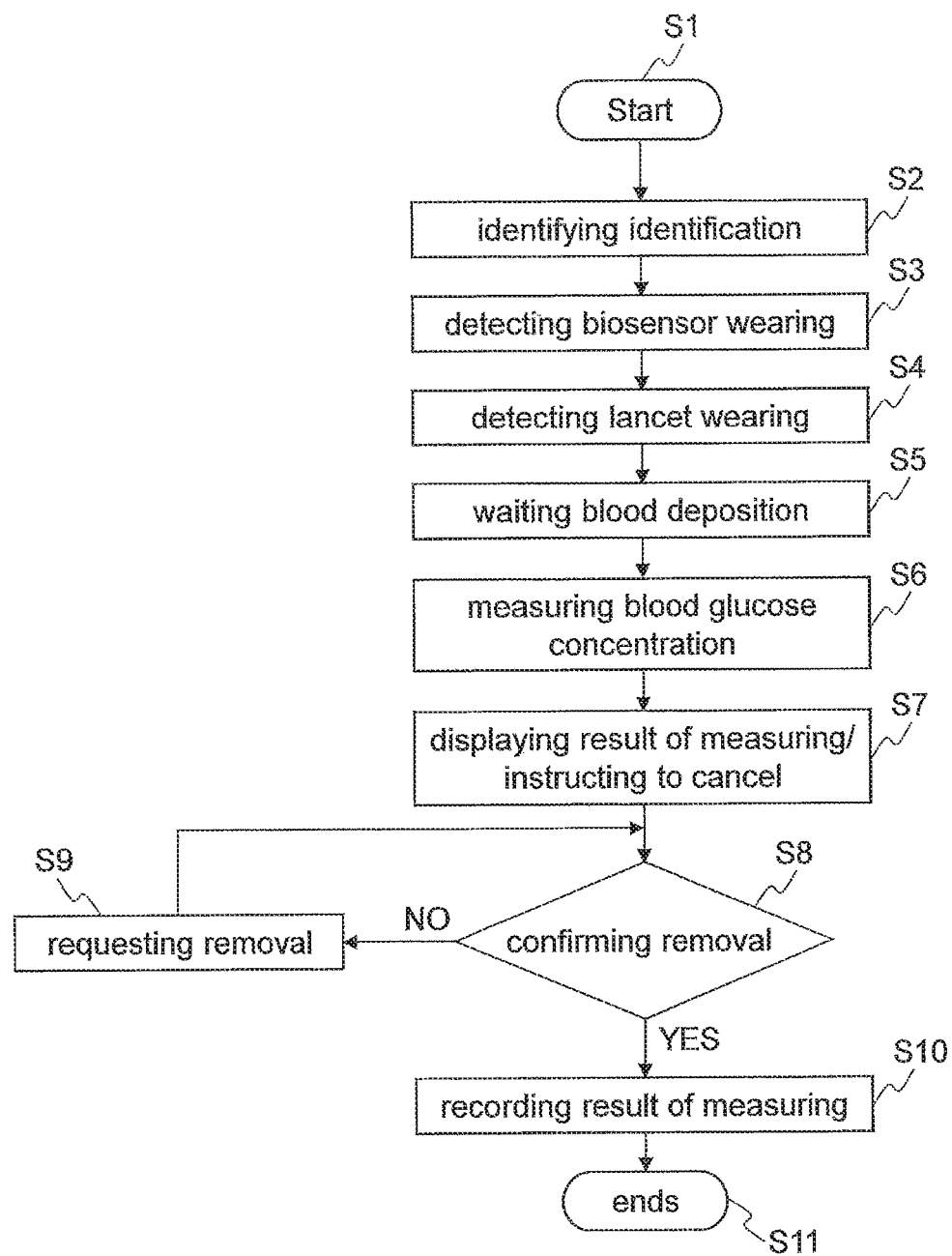
FIG. 6 is a flowchart showing movements of the liquid sample measurement device.

Next, the movement of the liquid sample measurement device, as arranged in a way described above, is described by referring to a flowchart of FIG. 6.

In step S1, the liquid sample measurement device starts processing measuring the blood glucose concentration in response to the operation of the user. For example, the process of measuring starts, when the user selects a menu of measuring the blood glucose concentration from a list of menu displayed on the display section 2 by using the input section.

In step S2, the controller 37 processes identifying various identification. Here, the various identification includes three items which are user (measuring person) identification, patient (person to be measured) identification, and sensor (biosensor) identification. By identifying the various identification, the liquid sample measurement device can record "who", "whom", "by which biosensor", and "when" measures.

An example in which a barcode reader is equipped as the input section 3 for processing identifying the various identification is described. By the way, it is fine to employ the RF-ID as the input section 3 to read the various identification by close distance wireless communication. For example, when a chip for the RF-ID is enclosed in a name plate of the user or a bottle in which the biosensor 7 is enclosed, the process of identifying the various identification by reading it can be performed.

First, when the user selects starting measuring the blood glucose concentration at the step S1, the display section 2 displays the instruction of reading the user identification. The user reads by using the barcode reader the barcode which is printed on the name plate and in which his/her information is recorded. The information of the user read by the barcode reader is transmitted to the controller 37.

The controller 37 reads from a list in which the information of the user is stored from the recording section 39. The controller 37 confirms whether or not the information of the user is included in the list in which the information of the user is stored. At this time, the controller 37 communicates with a server outside, when the information of the user is not included in the list. Then, the controller 37 confirms whether or not the information of the user exists in the server.

Here, for example, the server outside can be a computer which administrates users at each medical department at a hospital, or can be a server that administrates the users in the hospital entirely. Other than that, the server outside can be in any style as long as handling the information of the user, such as a server administrating the user who measures in medical institutions.

When the information of the user input by the input section 3 matches the information of the user stored in the recording section 39 or in the server, the user identification is identified to proceed to the next identification. At this time, when the user identification is identified by communicating with the server outside, the communication section 38 received the information of the user from the server, and the information is added to the list of the recording section 39 by the controller 37.

On the other hand, when the information matching the information of the user input by the input section 3 does not exist in both the recording section 39 and the server outside, the display section 2 displays a warning that the information of the user is wrong or that the user does not have authorization to measure. Then, it is prohibited from proceeding to a next process thereafter.

When the user identification goes through in a normal way, the controller 37 identifies the sensor identification next. Identifying the sensor identification is performed by reading enclosing material such as a bottle in which the biosensor is enclosed, or the barcode which is printed on the biosensor itself.

As the user identification, identifying the sensor identification having been read is performed by confirming whether or not matching with information (sensor identification) in a list prepared in the recording section 39, or the server outside. Further, for the biosensor 7 which is confirmed to match, the biosensor is confirmed whether or not a period of use thereof exceeds, by the controller 37 using the sensor identification. Further, at this time, it is fine that the controller 37 confirms whether or not there is recall information regarding the period of use and the like for the biosensor 7 having been identified, by inquiring the server outside via the communication section 38.

When the biosensor 7 is confirmed to be valid for measuring by identifying the sensor identification next, it proceeds to identifying patient identification next. On the other hand, when the information of the biosensor 7 is missing, or when the biosensor is identified to be invalid for measuring, the controller 37 displays a warning to use a different biosensor 7 by the display section 2. The controller 37 renews the list of the recording section 39, when receiving new information from the server outside with regards to the sensor identification having been read.

It is fine that the controller 37 encourages the user to confirm by showing the nitrification result by the display section 2 each time when identifying these identifications is completed. It is fine that the display section 2 switches displaying each time identifying the identification, or the display section 2 displays all together in line.

When identifying the user identification and the sensor identification is completed in a normal way, the user is prepared. With the preparation up to here, identifying the biosensor 7 is completed for one user using one lot of the biosensor 7. One lot of the biosensor 7 shows, for example, a plurality of sheets of the biosensor 7 enclosed in the bottle, the same characteristic, and the same production data.

For example, it is possible for a nurse to measure continuously the blood glucose concentration of a plurality of patients in a room of a hospital. Also, there is a case in which measuring for the plurality of patients continuously by changing the biosensor 7 enclosed in the same biosensor 7. In these ways, it is possible for the liquid sample measurement device to identify the patient identification, after identifying the user identification and the sensor identification once and omitting identifying thereafter.

In this case, it is possible to make the user identification and the sensor identification having been identified to be valid for a prescribed period of time. In other words, the prescribed period of time elapses after identifying the user identification and the sensor identification is completed, measuring can not performed without the user identification and the sensor identification are identified again. The prescribed period of time is preset by the user, a part administrating the liquid sample measurement device, or the like.

After identifying the user identification and the sensor identification is completed or selecting continuous measuring, which is described hereinafter, the display section 2 displays an instruction of reading the patient identification. Thereafter, it process to a patient's (subject person) preparation.

The user uses the barcode reader as the input section 3 to read the barcode indicating particular information of the patient. The barcode is printed on a strap worn by the patient (subject person) around a wrist or the like, the patient name plate configured at a bedside of the patient, or a medical chart or the like given to the patient.

The controller 37 reads out a patient table from the recording section 39. The controller 37 confirms whether or not the information of the patient, which is read by the barcode, in the patient table which is read. When the information of the patient is not included, the controller 37 forms a recording area for the patient newly read from the patient table, and is prepared to record the measured value of the blood glucose concentration. After the preparation is completed, the controller 37 makes the display section 2 to display encouraging wearing the biosensor 7 on the sensor wearing part 5, and the proceeds to the next step.

At step S3, the liquid sample measurement device confirms whether or not the biosensor 7 is equipped. When the sensor wearing detecting section 5b detects that the biosensor 7 is equipped on the sensor wearing part 5, the detection result is transmitted to the controller 37. In response to this, the controller 37 displays this thing on the display section 2. At this time, it is fine that the user confirms by seeing or the like validity of the biosensor 7 again by displaying the information of the biosensor 7 extracted in identifying the sensor identification at step S2.

At step S4, the liquid sample measurement device confirms whether or not the lancet device 8 is equipped. The controller 37 inquires whether or not the lancet device 8 is equipped, after detecting that the biosensor 7 is equipped. The lancet wearing detecting section 6a confirms whether or not the lancet device is equipped on the lancet wearing part 6, and transmits the result to the controller 37.

When the lancet device is not equipped, detecting by the lancet wearing detecting section 6a is continuously performed until step S6. When the lancet device 8 is detected to be equipped during step S8, a notice is sent to the controller 37 as an interrupting signal.

Subsequently, the controller 37 instructs the measuring section 36 to measure the blood glucose concentration in step S5. The measuring section 36 applies electric voltage on the connector 5a, and starts monitoring response electric current. Then, a state of holding measuring is maintained, until a fact that the blood is deposited on the biosensor 7 is electrically detected via the connector 5a by it.

At the same time, on the basis of the result for the inquiry to the lancet wearing detecting section 6a at step S4, the controller 37 makes the display section 2 display, as follows.

When the lancet device 8 is detected to be equipped by the lancet wearing detecting section 6a, the display section 2 displays performing puncturing by the lancet device 8 having being equipped, and depositing the blood having been squeezed on the biosensor 7.

When the lancet device 8 is detected to be not equipped by the lancet wearing detecting section 6a, the display section 2 displays performing puncturing by a different lancet device 8, and thereafter displays depositing the blood having been squeezed on the biosensor 7. If, while displaying this, the notice by the interrupting signal from the lancet wearing detecting section 6a which is mentioned above is sent, it is switched to display performing puncturing by the lancet device 8 having been equipped.

At step S6, the liquid sample measurement device measures the blood glucose concentration. The measuring section 36 applies the electric voltage to the connector 5a from getting into the state of holding of step S5. After the blood is deposited on the sample depositing part 15a of the biosensor 7 reaches the detection electrode 19, the blood glucose concentration in the blood is measured by a measuring algorithm which is prescribed. Then, when measuring is completed, the measuring section 36 transmits the result of measuring the blood glucose concentration to the controller 37.

At step S7, the controller 37 makes the display section 2 display the blood glucose concentration which has been measured. Then, the controller 37 makes the display section 2 display instructing removing the biosensor, as the disposable element on which the blood is deposited, and display instructing disposing.

Moreover, when the lancet device 8 is detected to be equipped at step S4, the controller 37 makes the display section 2 display encouraging removing the lancet device 8.

When a prescribed period of time has elapsed (for example, 1 minute) after displaying at step S7, the controller 37 inquires the sensor wearing detecting section 5b whether or not the biosensor 7 is removed (step S8). Further, when the lancet device 8 is detected to be equipped at step S4, the controller 37 inquires the lancet wearing detecting section 6a whether or not the lancet device 8 is removed.

When either the biosensor 7 or the lancet device 8 is not removed, it proceeds to step S9 to display encouraging removing by the display section 2. And it proceeds to step S8 again.

By this, the controller 37 makes the display section 2, which display the result of measuring by the measuring section 36, display the result of measuring the blood glucose concentration and display encouraging replacing the lancet device 8 and the biosensor 7.

Both the biosensor 7 and the lancet device 8 are removed, not equipped, it proceeds to step S10.

Step S10 is a step in which the controller 37 records in the recording section 39 the blood glucose concentration which has been measured at step S6 and to which the user add various information by associates to the blood glucose concentration. At step S8, after detecting the biosensor 7 and the lancet device 8 are removed, the display section 2 displays again the information of the patient, the result of measuring the blood glucose concentration, and the time of measuring, and displays encouraging the user to confirm.

The display section 2 displays a list of various information which can be associated with the result of measuring the blood glucose concentration. By this, the user can select the various information to be associated by using buttons on the input section 3. The various information is information with regards to lifestyle habits of the patient which is associated with the blood glucose concentration before meal, after meal, of before sleep for example. Other various information can be information by which the user (nurse) confirms a state of the patient, such as medication, medical examination, and other vital information. Further, other various information can be information which other engaged persons including doctors can share. Moreover, other than displaying the list, the display section 2 displays things that the user inputs by using the input section 3.

As described above, the controller 37 recognizes the user identification and the sensor identification which have been identified at step S2 as the added information, with respect to the information in which the patient and the result of measuring the blood glucose concentration are associated with the various information. Such information is recorded as the result of measuring in a recording area of the recording section 39 corresponding to the patient identification.

At step S11, the chain of processing in measuring the blood glucose concentration, which starts in step S1, ends. Here, it possible to select one of continuing or ending measuring the blood glucose concentration. When continuing measuring the blood glucose concentration is selected, it proceeds to identifying in step S2. At this time, it is possible to select one of identifying both the sensor identification and the patient identification and identifying (continuously identifying) only the patient identification. Therefore, in step S2, whether or not omitting identifying the sensor identification is displayed only proceeding from step S11, and user can select.

In this regards, the user has to identify the sensor identification in the cases, as follows. For example, it can be a case in which the biosensor 7 which is used for measuring the blood glucose concentration next time is enclosed in a different bottle from the bottle used in a previous time. Also, it can be a case in which it is necessary to read the sensor identification to confirm the biosensor 7. Further, it can be a case in which the biosensor 7 itself is determined to read the sensor identification one by one.

When ending measuring the blood glucose concentration is selected, it is possible to select transmitting the result of measuring recorded in the recording section 39 to other devices such as the server outside via the communication section 38. At this time, it is possible that the controller 37 transmits from the communication section 38 not just the result of measuring last time, but the results of measuring in the past.

When transmitting is completed, the liquid sample measurement device goes back to the normal menu before starting measuring the blood glucose concentration at step S1, and waits for the user instructing. Alternatively, the liquid sample measurement device intends to reduce power consumption by performing the minimum functions, and proceeds to a sleep mode as it is.

Selecting each process in Step S11 is performed interactively by the controller 37 which controls the display section 2 and the input section 3.

As shown in the chain of the process, the liquid sample measurement device prohibits from proceeding to the next step unless the user removes the biosensor 7 and the lancet device 8 each time when the blood glucose concentration is measured.

Moreover, a disposable type of the lancet device 8 is used for puncturing. By this, the liquid sample measurement device cannot measure the blood glucose concentration next time by equipping again the lancet device 8 which has been used once. For this reason, the liquid sample measurement device makes it possible to replace the part, which is arranged to be in contact with the skin of the measuring subject person, each time when used. The liquid sample measurement device includes an arrangement which requires replacing the lancet device 8 which is equipped on the lancet wearing part 6 each time puncturing is performed and after used for puncturing the skin. Thus, according to the liquid sample measurement device, it is possible to encourage replacing the lancet device 8 as the element on which the liquid sample such as the blood or the like of the living subject is deposited.

Also, of the liquid sample measurement device, the controller 37 controls the measuring section 36. The controller 37 controls the measuring section 36 not to perform measuring for the next time until the lancet device 8 is replaced after the measuring section 36 measures. Therefore, according to the liquid sample measurement device, it is possible to replace the lancet device 8 as the element on which the liquid sample such as the blood or the like of the living subject.

Likewise, the liquid sample measurement device cannot measure the blood glucose concentration for the next time with the biosensor 7 equipped thereon which has been used once. Therefore, the liquid sample measurement device makes the part, which is arranged to be contact with the subject person, replaced certainly when used once. The liquid sample measurement device like this includes an arrangement which requires replacing the biosensor 7 which is equipped on the device main body 1 each time puncturing is performed and after used for puncturing the skin. Thus, the liquid sample measurement device encourages replacing the biosensor 7 as the element on which the liquid sample such as the blood or the like of the living subject is deposited.

Further, the liquid sample measurement device cannot record with the biosensor 7 and the lancet device 8 being equipped thereon which have been used once. For this reason, the liquid sample measurement device makes it possible to replace the part, which is arranged to be in contact with the skin of the measuring subject person, each time when used. The liquid sample measurement device like this includes an arrangement which requires replacing the biosensor 7 and the lancet device 8 each time puncturing is performed and after used for puncturing the skin. Thus, according to the liquid sample measurement device, it is possible to replace the biosensor 7 and the lancet device 8 as the elements on which the liquid sample such as the blood or the like of the living subject is deposited.

As mentioned above, according to the liquid sample measurement device, in an arrangement in which the element on which the blood is deposited is replaceable, it is possible to render the user to replace. As a result, contamination and infection by the blood being deposited are prevented.

Also, by equipping the lancet device 8 to the liquid sample measurement device, it is possible to decrease shaking when puncturing and to decrease pain of the user more than by using a very small lancet device 8 alone. In other words, when it is difficult to hold by hand the very small lancet device 8, equipping the lancet device on the relatively larger lancet device 8 makes it possible to hold firmly. Thus, since it is easier to handle the lancet device 8 and to be held stably by hand, shaking and fluctuation less likely happen. As a result, since the vibration on the puncturing needle becomes small by decreasing the vibration of the lancet device 8 when puncturing, the pain caused by the fluctuation of the puncturing needle is decreased.

As mentioned above, according to the liquid sample measurement device of the present embodiment, since it is easy to replace the biosensor 7 and the lancet device 8 which is disposable, the convenience is enhanced when replacing the element on which the blood is deposited.

Further, the liquid sample measurement device cannot measure newly the blood glucose concentration unless the element such as the biosensor 7 and the lancet device 8 on which the blood is deposited is replaced. For this reason, it is possible to contribute in preventing the infection by the deposited blood.

Additionally, according to the liquid sample measurement device, it results in decreasing the vibration when puncturing and decreasing burden of the user.

Further, a spring for puncturing as an element which wears much is that of the lancet device 8 which is deposable. By this, the liquid sample measurement device does not have to fix the spring for puncturing within the device main body 1. By this, since considering deterioration of the spring for puncturing because of multiple use of the spring for puncturing is not necessary, the liquid sample measurement device has merits of making the maintenance easy.

Further, according to the liquid sample measurement device, the result of measuring the blood glucose concentration and encouragement of replacing the lancet device 8 and the biosensor 7 are displayed and kept displaying until replacing. Therefore, according to the liquid sample measurement device, it is possible to encourage replacing the biosensor 7 and the lancet device 8 as the elements on which the liquid sample such as the blood or the like of the living subject.

Second Embodiment

Next, a second embodiment of the present invention is described by referring to the figures. For an ejecting mechanism of the biosensor 7 and the lancet device 8 configured within the liquid sample measurement device, it is different from the liquid sample measurement device of the first embodiment. By the way, for the liquid sample measurement device as in the second embodiment, the same configuration and movement as in the first embodiment is omitted by using the same symbols.

Figure 7:
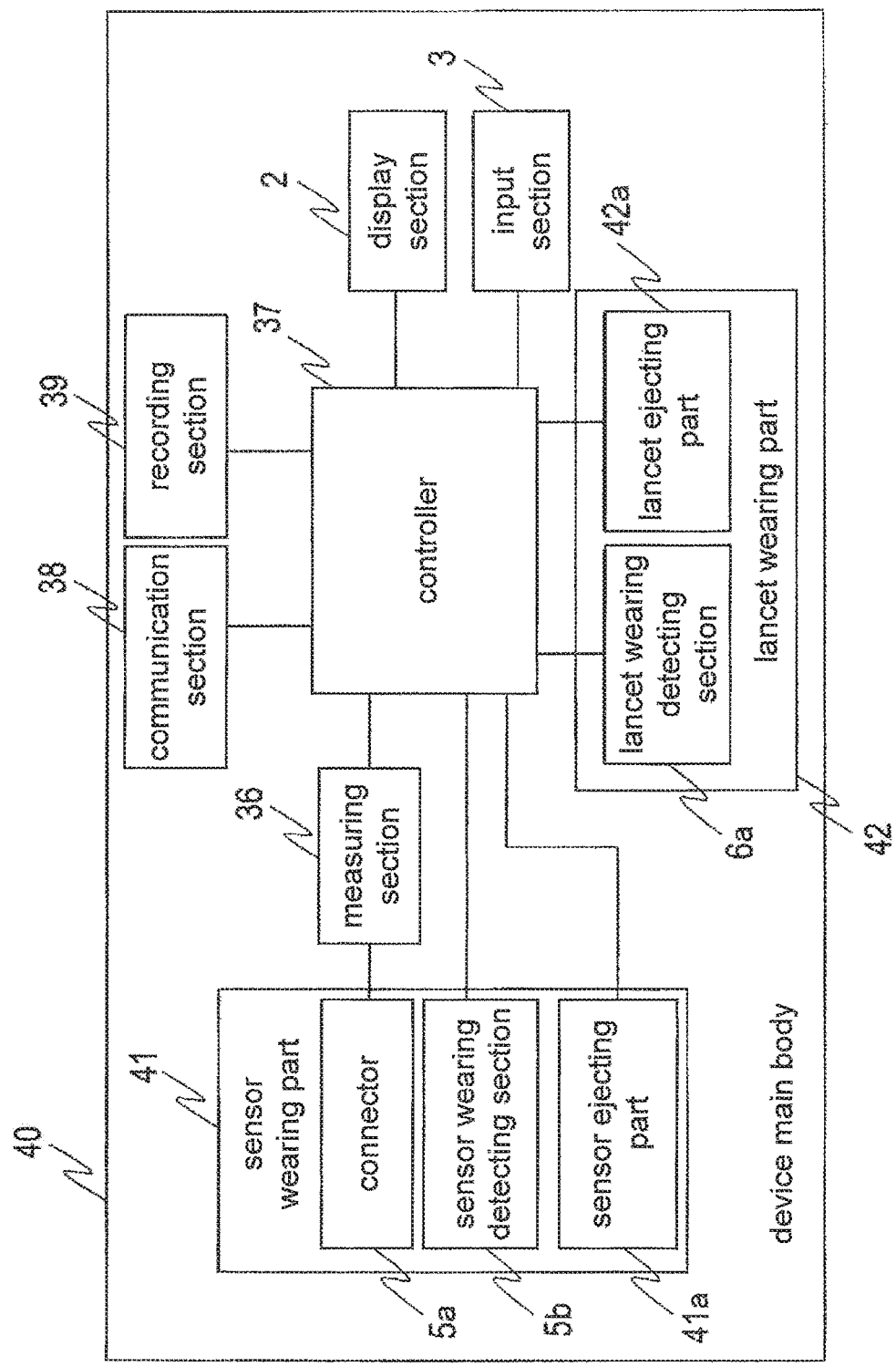
FIG. 7 is a block diagram showing the liquid sample measurement device of a second embodiment.

FIG. 7 is a block diagram which shown the liquid sample measurement device of the present embodiment. The embodiment shown in FIG. 5 is different in that a sensor ejecting part 41a is configured on a sensor wearing part 41, and a lancet ejecting part 42a is configured on a lancet wearing part 42.

The sensor ejecting part 41a is a sensor ejecting mechanism which pushes out the biosensor 7 equipped on sensor wearing part 41 and separate from the device main body 40. The sensor ejecting mechanism includes a pushing part and a drive motor. The pushing part pushes out an end of the biosensor from the inside to the outside of the device main body 40. The drive motor drives the pushing part. The sensor ejecting part 41a ejects, as pushing out, the biosensor 7 from the sensor wearing part 41 by controlling the drive motor, when the controller 37 instructs to eject the biosensor 7.

The lancet ejecting part 42a includes a lancet ejecting mechanism which pushes out the lancet device 8 being equipped on the lancet wearing part 42, and which separates from the device main body 40. The lancet ejecting mechanism includes a pushing part and a drive motor. The pushing part pushes out an end of the lancet device 8 from the inside to the outside of the device main body 40. The drive motor drives the pushing part. The lancet ejecting part 42a ejects, as pushing out, the lancet device 8 from the lancet wearing part 42 by controlling the drive motor, when the controller 37 instructs to eject the lancet device 8.

Because of these configurations, the next process is added to flow chart as FIG. 6 shows.

At step S7, at the same time or after measuring the blood glucose concentration on the display section 2, instructing of removing the biosensor 7 and the lancet device 8 is displayed. At this time, the display section 2 encourages the user to input, by using the input section 3, the instruction of removing the biosensor 7 and the lancet device 8 the text and illustration.

Then, when the instruction of removing the biosensor 7 and the lancet device 8 from the input section 3 is input, the controller 37 instructs the sensor ejecting part 41a and the lancet ejecting part 42a.

As mentioned above, instead of the user holding and pulling out the biosensor 7 and lancet device 8 which have been used, the liquid sample measurement device automatically ejects. By this, it is possible to dispose, without the user touching, the biosensor 7 and the lancet device 8 on which the blood is deposited.

The sensor ejecting part 41a and the lancet ejecting part 42a can be unitarily configured. The liquid sample measurement device ejects the biosensor 7 and the lancet device 8 at the same time, when the use instructs the biosensor 7 and the lancet device 8. In this case, because equipping and ejecting the biosensor 7 are dominant, the lancet wearing detecting section 6a and confirming equipping the lancet in step S4 can be omitted.

Third Embodiment

Figure 8:
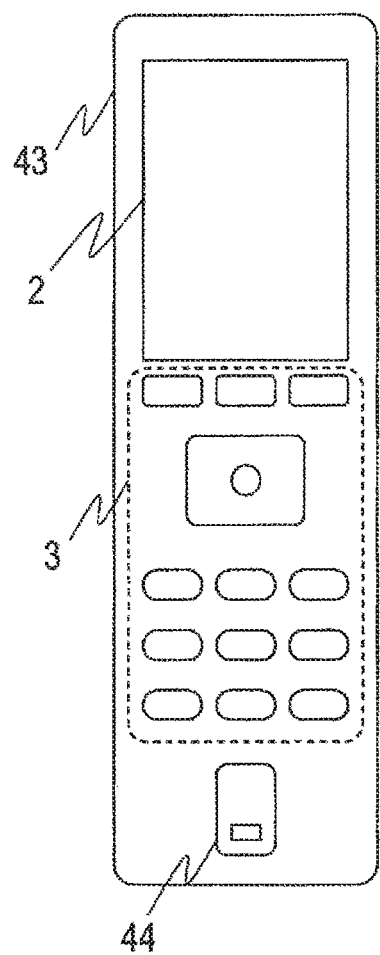
FIG. 8 is a view showing an arrangement of the liquid sample measurement device of a third embodiment.
Figure 9:
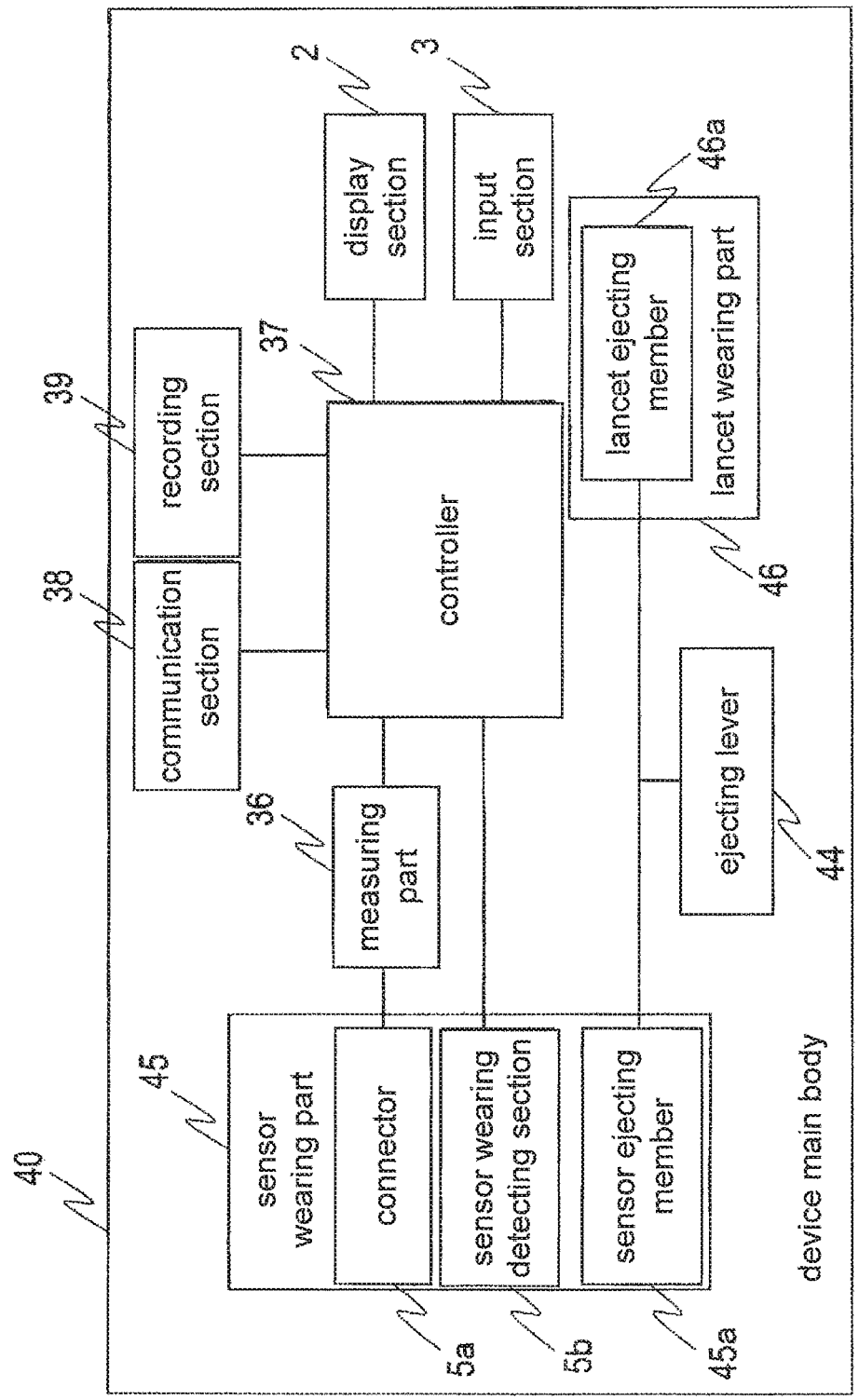
FIG. 9 is a block diagram showing the same liquid sample measurement device.

Next, the liquid sample measurement device shown as a third embodiment of the present invention by referring to the figures. The liquid sample measurement device of the third embodiment is different from the liquid sample measurement device of the first embodiment because of mechanism which ejects the biosensor 7 and the lancet device 8. The same configuration and movement as in the first embodiment is omitted by using the same symbols FIG. 8 is a view (front view) of the liquid sample measurement device of the present embodiment. Also, a block diagram of the liquid sample measurement device is shown in FIG. 9. The liquid sample measurement device is different from the liquid sample measurement device shown in FIGS. 1A to 1C because an ejecting lever 44 which the user operates is configured on a lower side of the device main body 43.

The ejecting lever 44 is slid by the user in a longitudinal direction of the device main body 43. A sensor ejecting member 45a and the lancet ejecting member 46a are connected to the rejecting lever 44. The sensor ejecting member 45a pushes out the biosensor 7 on the sensor wearing part 45. The lancet ejecting member 46a pushes out the lancet device 8 on the lancet wearing part 46. Therefore, when the user slides the ejecting lever 44, the biosensor 7 and the lancet device 8 are ejected from the device main body 43.

Figure 10:
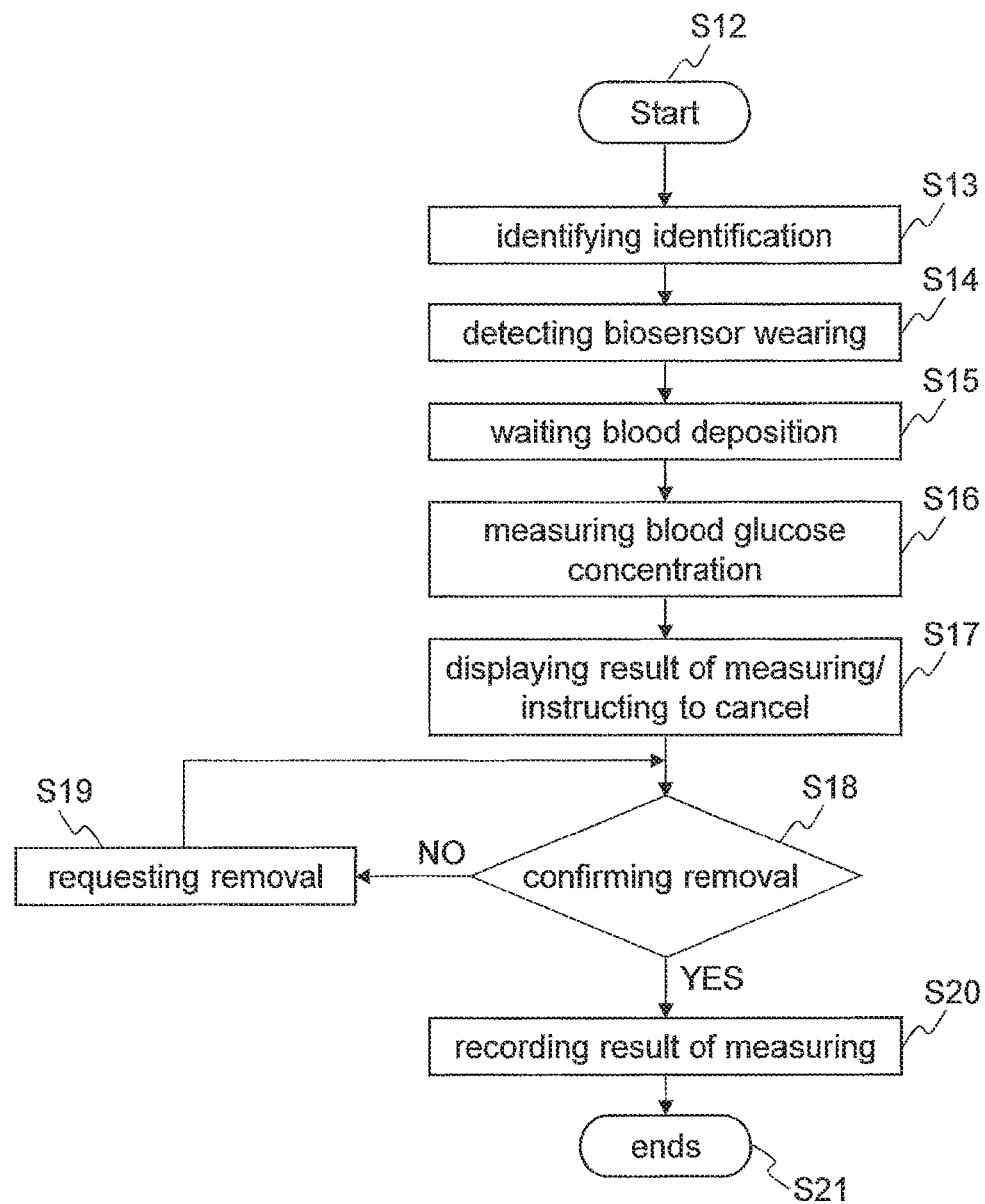
FIG. 10 is a flowchart showing movements of the same liquid sample measurement device.

FIG. 10 is a flowchart that shows the movement of the liquid sample measurement device of the present embodiment.

At step S12, the liquid sample measurement device starts measuring the blood glucose concentration. The step is same as step S1 in FIG. 6.

At step S13, the controller 37 performs the identification process for various identification. The step is same as step S2 in FIG. 6.

At step S14, the controller 37 confirms whether or not the biosensor 7 is equipped. The step is same as step S3 in FIG. 6.

At step S15, the controller 37 starts holding measuring the blood glucose concentration. The step is almost same as step S5 in FIG. 6. In this regards, the display section 2 is only different for displaying the instruction of depositing the blood on the biosensor 7.

Step S16 is a step for measuring the blood glucose concentration. The step is same as step S6 in FIG. 6.

At step S17, the controller 37 makes the display section 2 display the blood glucose concentration being measured, and display the disposal by operating the ejecting lever 44 to remove the biosensor 7.

Then, the liquid sample measurement device asks ejecting (removing) at steps S18 and S19, after confirming that the biosensor 7 is ejected (removed). This is same as steps S8 and S9 in FIG. 6. As mentioned above, the biosensor 7 and the lancet device 8 are ejected at the same time by operating the ejecting lever 44. Thus, when the biosensor 7 is detected as being removed (ejected) on the basis of the signal of the sensor wearing detecting section 5b, the controller 37 assumes that likewise the lancet device 8 is removed. Also, when the biosensor 7 is detected as being removed on the basis of the signal of the lancet wearing detecting section 6a, it is fine that the controller 37 assumes that likewise the biosensor 7 is removed. Then, it proceeds to a next process of step S20.

At step S20, the controller 37 records the result of measuring the blood glucose concentration on the recording section 39. The step is same as step S10 in FIG. 6.

At step S21, the chain of the process ends. The step is same as step S11 in FIG. 6.

In this manner, unless the biosensor 7 and the lancet device 8, which are the disposable elements, are removed, it works not proceeding to the next measuring of the blood glucose concentration by watching the ejection of the biosensor 7. Therefore, according to the liquid sample measurement device, it is possible to replace the elements on which the liquid sample such as the blood of the living subject is deposited.

As the device main body 1, 40, 43 can be equipped even though the shape of the lancet device 8 is different from the one in FIGS. 4A and 4B, it is fine to include an adaptor between the lancet device 8 and the device main body 1, 40, 43. The adaptor is detachable to the device main body 1, 40, 43, and is fine either being disposable after used one time or being usable for multiple times. Also, the adaptor can be a part of the cover which covers partially or entirely the device main body 1, 40, 43. For example, the cover covers at least the surface, on which the lancet device 8 is equipped, of the device main body 1, 40, 43. Also, an end of the cover can extend from the upper part of the input section 3 to the upper part of the display section 2. Further, the cover prevents fluid such as the blood from depositing directly on the device main body 1, 40, 43.

Fourth Embodiment

Figure 11:
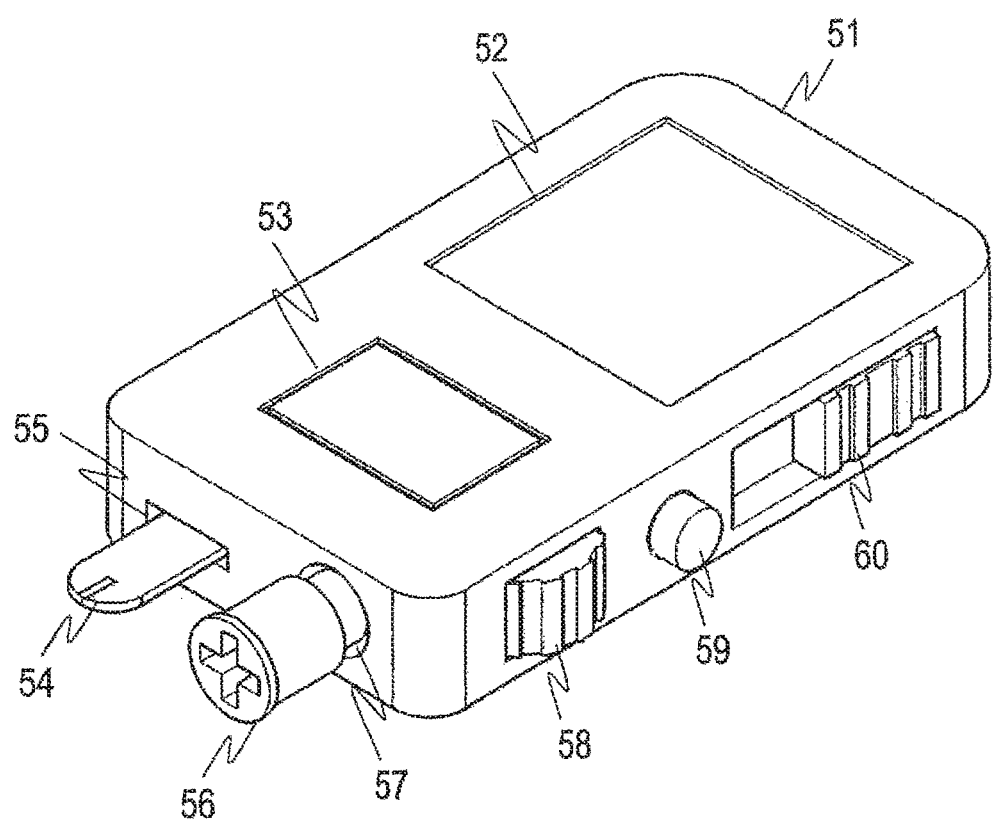
FIG. 11 is a view showing an arrangement of the liquid sample measurement device of a fourth embodiment.

FIG. 11 is a view showing the liquid sample measurement device of a fourth embodiment. The liquid sample measurement device of the present embodiment includes a puncturing needle cartridge 56 which is disposable and conventional, as the lancet device. The puncturing needle cartridge 56 which is disposable is equipped to a device main body 51 instead of the lancet device which is disposable. Drive mechanism is equipped in the device main body 51 for puncturing. It is different from the liquid sample measurement device of the first embodiment for these issues. The elements of the present embodiment which constitute the liquid sample measurement device and which are not described are in the same configuration and for the same movement described in the first embodiment.

As shown in FIG. 11, the liquid sample measurement device includes a display section 52 and an input section 53 on the front side of the device main body 51. Further, the liquid sample measurement device includes a sensor wearing part 55 on which a biosensor 54 is equipped on the side of the device main body 51, and a lancet wearing part 57 on which a puncturing needle cartridge 56 is equipped. Further, a puncturing depth adjusting part 58, a puncturing button 59, and an ejecting lever 60 are configured on the other side of the device main body 51. The puncturing depth adjusting part 58 is mechanism which adjusts depth of puncturing when puncturing is performed by using the puncturing needle cartridge 56 equipped on the lancet wearing part 57. The puncturing button 59 is button mechanism for puncturing by using the puncturing needle cartridge 56. The ejecting lever 60 includes mechanism which ejects at least the puncturing needle cartridge 56 from the lancet wearing part 57.

The configuration and the movement of the biosensor 54 and the sensor wearing part 55 are same as the biosensor 54 and the sensor wearing part 5 shown in the first embodiment.

Figure 12B:
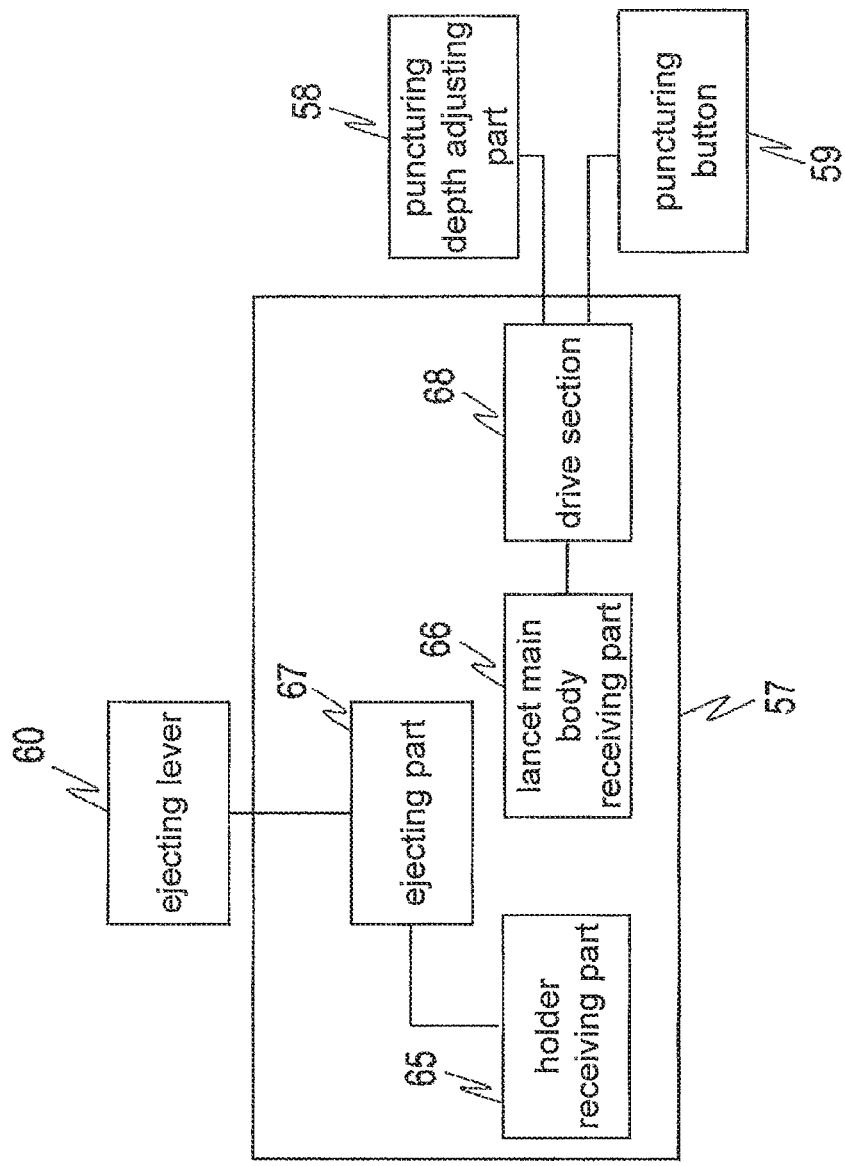
FIG. 12B is a block diagram showing relationship of a lancet wearing part configured on a device main body with peripheral elements.
Figure 12A:
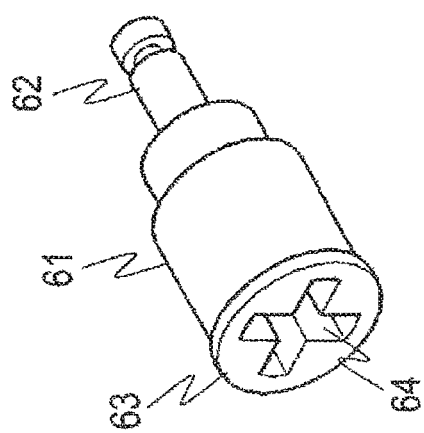
FIG. 12A is a diagonal view showing a puncturing needle cartridge.
Figure 13:
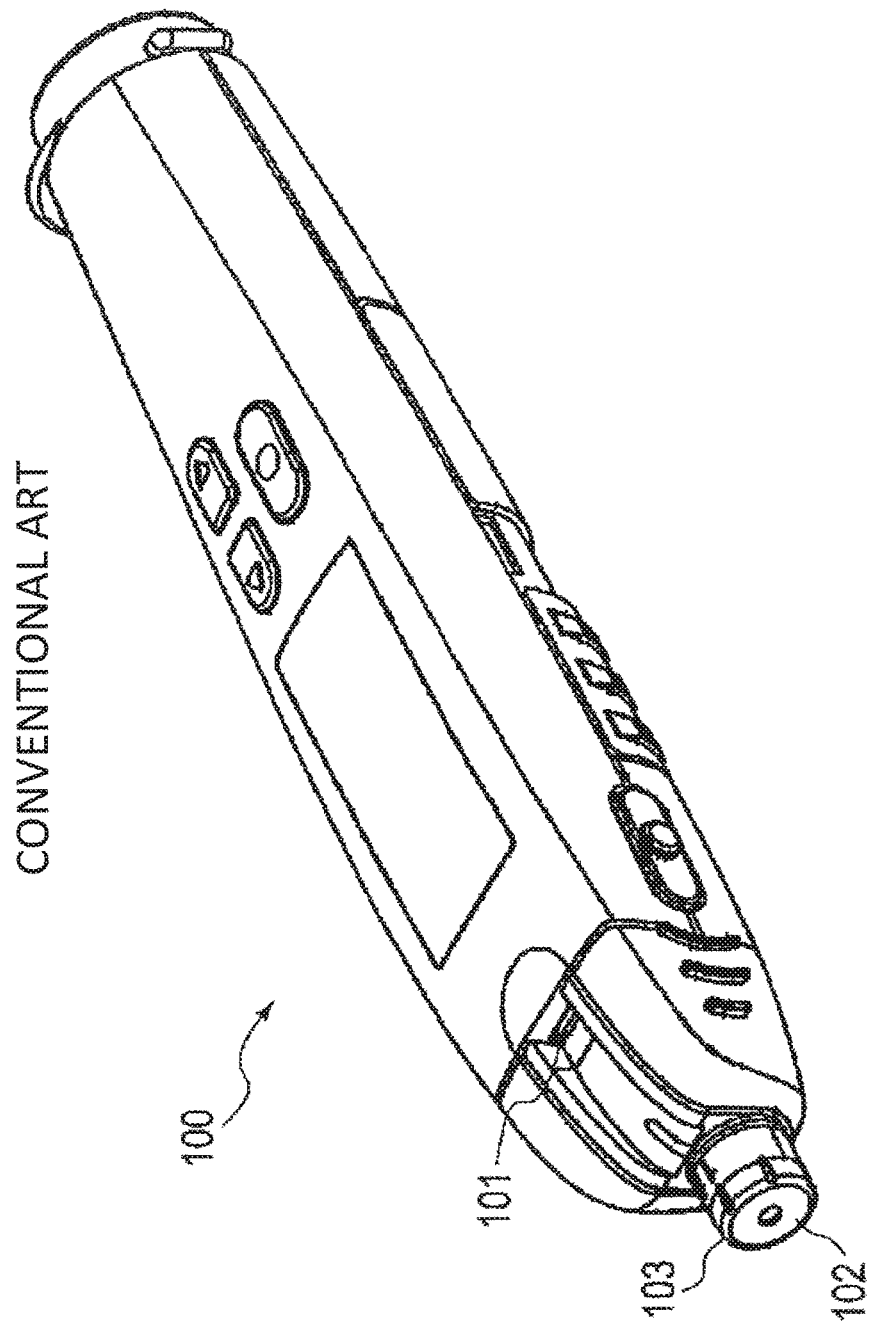
FIG. 13 is a view showing an arrangement of a conventional liquid sample measurement device.

The puncturing needle cartridge 56 is, for example, the one disclosed in aforementioned Patent Literature 4. A simplified view of the puncturing needle cartridge 56 is shown in FIG. 12A. As shown in Patent Literature 4, a lancet main body 62 is embedded on the puncturing needle cartridge 56 in a hollow part inside a puncturing needle holder 61. The lancet main body 62 is slidable in the hollow part of the puncturing needle holder 61. A puncturing needle is configured (not shown in the figures) on a tip of the lancet main body 62. The puncturing needle sticks out from an opening part 64 configured on a skin contacting part 63 of the puncturing needle holder 61 and performs puncturing against the skin. FIGS. 12A and 12B omit showing other configuration such as a protective cap of the puncturing needle in FIGS. 12A and 12B.

FIG. 12B is a block diagram showing relationship between the lancet wearing part 57 on the device main body 51 and peripheral elements. In the lancet wearing part, a holder receiving part 65 and lancet main body receiving part 66 are configured. The holder receiving part 65 holds the puncturing needle holder 61 when the puncturing needle cartridge 56 is inserted. The lancet main body receiving part 66 sustains the lancet main body. Further, the lancet wearing part 57 includes an ejecting part 67 which is mechanism to eject the puncturing needle cartridge 56 from the lancet wearing part 57 by pushing out the puncturing needle holder 61 sustained by the holder receiving part 65. Also, the lancet wearing part 57 includes a drive unit 68 which is mechanism for puncturing by driving the lancet main body 62 via lancet main body receiving part 66 by operating the puncturing button 59. The drive unit 68 is arranged to adjust the depth of puncturing by changing sticking amount of the puncturing needle by operating the puncturing depth adjusting part 58.

When the user inserts the puncturing needle cartridge 56 in the lancet wearing part 57, an end of the lancet main body 62 is in contact with the lancet main body receiving part 66 and sustained. When the user keep inserting the puncturing needle cartridge 56, subsequently an end of the puncturing needle holder 61 is in contact with the holder receiving part 65 and sustained. From when the end of the lancet main body 62 is sustained by the lancet main body receiving part 66 to when the end of the puncturing needle holder 61 is sustained by the holder receiving part 65, the lancet main body receiving part 66 is pushed by receiving a force from the user via the lancet main body 62.

A spring (not shown in the figures) configured on the drive unit 68 is charged (compressed) by the movement of the lancet main body receiving part 66 being pushed in. As a result, a drive force is stored in the drive unit 68 and the preparation of puncturing is completed, when the puncturing needle cartridge 56 is equipped on the lancet wearing part 57.

Thereafter, when the user instructs to perform puncturing by pushing the puncturing button 59, the drive unit 68 performs puncturing by driving the lancet main body 62 by the drive force stored.

When the user instructs to eject the puncturing needle cartridge 56 by operating the ejecting lever 60, the ejecting part 67 works as pushing out the end of the puncturing needle holder 61 in order to release the sustention by the holder receiving part 65. In other words, the puncturing needle cartridge 56 pushes out the puncturing needle holder 61 in a direction towards outside from the device main body 51 which is opposite to the direction of inserting the puncturing needle cartridge 56 to the lancet wearing part 57. At this time, the lancet main body 62 is arranged to be pulled by the puncturing needle holder 61. The sustention by the lancet main body receiving part 66 of the puncturing needle holder 61, as the sustention by the holder receiving part 65 of the puncturing needle holder 61 is released.

In this manner, the liquid sample measurement device of the present embodiment includes mechanism to drive the puncturing needle cartridge 56. When puncturing by using the puncturing needle cartridge 56, the user makes the skin contacting part 63 of the puncturing needle cartridge 56 in contact with the part for puncturing. The puncturing needle cartridge 56 cannot be reused after puncturing one time. Thus, the liquid sample measurement device of the present embodiment prevents infection due to the blood which is deposited because parts on which the blood is easily deposited are certainly replaced, each time after the blood glucose concentration is measured.

The sensor ejecting member 45a can be configured on the sensor wearing part 55 as shown in the third embodiment. When the user operates the ejecting lever 60, not only the puncturing needle cartridge 56, but also the biosensor 54 is ejected by the sensor ejecting member 45a, and separated from the device main body 51. Here, the sensor ejecting member 45a works as pushing the end of the biosensor 54 towards outside of the device main body 51m by synchronizing with the movement of the ejecting lever 60.

In all the embodiments described above, measuring the blood glucose concentration is described as an example, but not limited to it. For example, not only the blood glucose concentration, it is also fine as long as measuring by the biosensor equipped on the apparatus, such as value of lactic acid or cholesterol, and not limited to the subject person.

Moreover, for the biosensor, it is not limited by the measuring method, but it is still fine as long as the biosensor is disposable, not only the electrochemical method, but also optical method and the like.

The entire contents of Japanese Patent Application No. 2011-283196 (filed on Dec. 26, 2011) is incorporated herein by reference.

The aforementioned embodiment is an example of the present invention. For this, the present invention is not limited to the aforementioned embodiment, but can have different embodiments. Needless to say, it is possible to make various modifications depending on the designs, as long as the modifications do not deviate from technical ideas of the present invention.

INDUSTRIAL APPLICABILITY

The aforementioned liquid sample measurement device can be useful for a heath care monitoring apparatus, and the like, which measures body fluid.

The invention claimed is:

1. A liquid sample measurement device to which a biosensor may be removably attached, the biosensor having a blood sample deposited on it created by a puncturing of a skin, the liquid sample measurement device comprising:
a sensor port to which the biosensor is removably attached;
a measuring sensor configured to measure an amount of a substance in the blood sample by applying a voltage or a current to electrodes of the biosensor, and to produce a first measurement indicating the measured amount of the substance in the blood sample; and
a display configured to display the first measurement; a sensor detector configured to detect whether or not the biosensor is attached to the liquid sample measurement device;
a memory configured to record the first measurement; and
a controller configured to control the measuring sensor, wherein the controller receives a result of the detection from the sensor detector after the measuring sensor produces the first measurement, the controller controls the display to continuously display an instruction for removing the biosensor unless a user removes the biosensor from the liquid sample measurement device, and the controller prohibits recording the first measurement in the memory unless the user removes the biosensor from the liquid sample measurement device.

2. The liquid sample measurement device according to claim 1, wherein the controller inquires the sensor detector whether or not the biosensor is removed after a prescribed period of time has elapsed.

3. The liquid sample measurement device according to claim 1, further comprising:
a user interface configured to accept user input of information of the user and the biosensor,
wherein the controller prohibits the measuring sensor from measuring the amount of the substance in the blood sample unless the user input of information input to the user interface is valid.

* * * * *